US010111595B2

(12) United States Patent
Wundrak et al.

(10) Patent No.: US 10,111,595 B2
(45) Date of Patent: Oct. 30, 2018

(54) METHOD FOR CHECKING TOOTH POSITIONS

(71) Applicant: Sirona Dental Systems GmbH, Bensheim (DE)

(72) Inventors: Stefan Wundrak, Gronau (DE); Kai Lindenberg, Wersau (DE)

(73) Assignee: Sirona Dental Systems GMBH, Bensheim (DE)

( * ) Notice: Subject to any disclaimer, the term of this patent is extended or adjusted under 35 U.S.C. 154(b) by 413 days.

(21) Appl. No.: 14/410,914

(22) PCT Filed: Jun. 25, 2013

(86) PCT No.: PCT/EP2013/063196
§ 371 (c)(1),
(2) Date: Dec. 23, 2014

(87) PCT Pub. No.: WO2014/001284
PCT Pub. Date: Jan. 3, 2014

(65) Prior Publication Data
US 2015/0342464 A1    Dec. 3, 2015

(30) Foreign Application Priority Data

Jun. 25, 2012    (DE) .................. 10 2012 210 758

(51) Int. Cl.
*A61C 5/00* (2017.01)
*A61B 5/00* (2006.01)
(Continued)

(52) U.S. Cl.
CPC ............ *A61B 5/0088* (2013.01); *A61B 5/055* (2013.01); *A61B 5/742* (2013.01); *A61B 6/032* (2013.01);
(Continued)

(58) Field of Classification Search
CPC .......... A61B 5/0088; A61B 5/055; A61B 6/14; A61B 6/032; A61B 6/5217; A61B 5/742;
(Continued)

(56) References Cited

U.S. PATENT DOCUMENTS 5,368,478 A * 11/1994 Andreiko ................. A61C 7/00
433/24
5,604,817 A * 2/1997 Massen .................... A61C 9/00
348/66
(Continued)

FOREIGN PATENT DOCUMENTS

DE      102 50 006 A1    5/2004
DE   10 2007 001 684 A1    8/2008

OTHER PUBLICATIONS

Office Action dated Feb. 13, 2013, in German Patent Application No. 10 2012 210 758.4.
(Continued)

*Primary Examiner* — Garrett Atkinson
(74) *Attorney, Agent, or Firm* — Fitzpatrick, Cella, Harper & Scinto

(57) ABSTRACT

The invention relates to a method for checking tooth positions, wherein an initial three-dimensional volume exposure (1) of teeth (2, 3, 4) to be checked is implemented, wherein the position and orientation of the teeth (2, 3, 4) to be checked are determined based on the initial volume exposure (1); wherein the teeth to be checked are natural teeth (2, 3, 4) comprised of tooth stumps (6, 7, 8) and tooth roots (9, 10, 11) and/or are artificial teeth comprised of artificial tooth stumps and implants; wherein the positional relationship and orientation of the tooth stumps (6, 7, 8) relative to the tooth roots (9, 10, 11) and/or to the implants are determined in particular. For checking, a first optical surface monitoring exposure (25) of the teeth (2, 3, 4) is implemented, wherein using the positional relationship thus determined the posi- (Continued)

tion and orientation of the tooth roots (9, 10, 11) and/or of the implants relative to one another and/or relative to a jawbone (5) are determined based on the position of the surfaces (13, 14, 15) of the tooth stumps (6, 7, 8) from the optical surface monitoring exposure (25).

19 Claims, 2 Drawing Sheets

(51) Int. Cl.
*A61B 5/055* (2006.01)
*A61B 6/03* (2006.01)
*A61B 6/14* (2006.01)
*A61C 9/00* (2006.01)
*A61C 8/00* (2006.01)
*A61B 6/00* (2006.01)
*A61C 7/00* (2006.01)

(52) U.S. Cl.
CPC .............. *A61B 6/14* (2013.01); *A61B 6/5217* (2013.01); *A61C 7/002* (2013.01); *A61C 8/0096* (2013.01); *A61C 9/006* (2013.01); *A61C 9/0053* (2013.01); *A61C 2007/004* (2013.01)

(58) Field of Classification Search
CPC ..... A61C 8/0096; A61C 9/006; A61C 9/0053; A61C 7/002; A61C 2007/004
USPC ................. 433/29–31, 68–71, 213–225, 229
See application file for complete search history.

(56) References Cited

U.S. PATENT DOCUMENTS

| | | | |
|---|---|---|---|
| 7,367,801 B2 | 5/2008 | Saliger | |
| 8,727,776 B2* | 5/2014 | Mehl | A61C 13/0004 433/223 |
| 8,798,346 B2 | 8/2014 | Cizek | |
| 2004/0015327 A1 | 1/2004 | Sachdeva et al. | |
| 2004/0029068 A1* | 2/2004 | Sachdeva | A61C 7/00 433/24 |
| 2004/0197727 A1 | 10/2004 | Sachdeva et al. | |
| 2006/0063135 A1* | 3/2006 | Mehl | A61C 13/0004 433/223 |
| 2009/0325127 A1 | 12/2009 | Kusch et al. | |
| 2011/0268327 A1 | 11/2011 | Getto et al. | |

OTHER PUBLICATIONS

International Preliminary Report on Patentability, PCT/EP2013/063196, dated Dec. 31, 2014.
International Search Report dated Oct. 25, 2013, in PCT/EP2013/063196.

\* cited by examiner

METHOD FOR CHECKING TOOTH POSITIONS

CROSS-REFERENCE TO RELATED APPLICATIONS

This application is a national stage entry of International Application No. PCT/EP2013/063196 filed Jun. 25, 2013, which claims priority to German Patent Appln. No. 10 2012 210 758.4 filed Jun. 25, 2012.

BACKGROUND OF THE INVENTION

Field of the Invention

The invention relates to a method for checking tooth positions, wherein an initial three-dimensional volume exposure of teeth to be checked is implemented, wherein the position and orientation of teeth to be checked are determined on the basis of the initial volume exposure. The teeth to be checked are thereby natural teeth consisting of tooth stumps and roots, and/or artificial teeth consisting of artificial tooth stumps and implants, wherein in particular the positional relationship and orientation of the tooth stumps relative to the tooth roots and/or to the implants are determined.

Description of the Related Art

Several methods for tracking tooth positions over time are known from the prior art, wherein three-dimensional x-ray acquisition methods such as CT acquisition methods are most often used. The tooth positions are then checked on the basis of the generated x-ray exposures.

The disadvantage of these methods is that, based on the dose load due to the x-ray radiation, frequent observations of tooth positions often cannot be justified.

The object of the present invention is therefore to provide a method for checking tooth positions which will permit frequent monitoring with a low dose load.

BRIEF SUMMARY OF THE INVENTION

The invention relates to a method for checking tooth positions, wherein an initial three-dimensional volume exposure of teeth to be checked is implemented, wherein the position and orientation of the teeth to be checked are determined on the basis of the initial volume exposure. The teeth to be checked are thereby natural teeth consisting of tooth stumps and tooth roots, and/or artificial teeth consisting of artificial tooth stumps and implants. In particular the positional relationship and orientation of the tooth stumps relative to the tooth roots and/or to the implants are thereby determined. To check the tooth positions over a longer period of time at regular time intervals, at least one first optical surface monitoring exposure of the teeth is subsequently implemented, wherein the position and orientation of the tooth roots and/or of the implants relative to one another and/or relative to a jawbone are determined using the positional relationship thereby determined, based on the position of the surfaces of the tooth stumps from the optical surface monitoring exposure.

The positional relationship is determined automatically in a computer-assisted process, wherein the tooth stumps, the tooth roots and/or the implants are registered automatically using a segmentation method and then the positional relationship is determined automatically in a computer-assisted process. 3D models of the segmented teeth are subsequently rotated and/or displaced until the surfaces of the tooth stumps of these 3D models are brought into superposition with the surfaces of the tooth stumps from the optical surface monitoring exposure.

The basic idea of the present method lies in the assumption that the shape of the individual teeth remains unchanged, and only the position and orientation of the teeth and their tooth roots relative to the jawbone are changed. Consequently, the position and orientation of the tooth root can be calculated from the position of the surfaces of the tooth roots from the optical surface monitoring exposure.

It is necessary to check tooth positions over a longer period of time primarily given dental corrections by means of dental braces which correct, for example, a malocclusion, cross bite, overbite or malformation of the teeth or the jaw. The initial three-dimensional volume acquisition may be performed by means of a CT x-ray apparatus or an MRT device, for example. The initial volume exposure thereby created can then subsequently be analyzed by means of a segmentation method, and the teeth (comprising tooth stumps and tooth roots or, respectively, implants) can be segmented and subsequently registered. The three-dimensional optical surface monitoring acquisition can be performed, for example, by means of a strip projection method using a dental camera or also by means of a digitized impression. A digitized impression is thereby a three-dimensional image of a plastic tooth/bite impression of the dental subject, wherein the measurement can be performed using the strip projection method, by CT measurement, by MRT measurement or by mechanical scanning.

In calculation of the position of the tooth roots and/or of the implants, for example, 3D models of the segmented teeth from the initial volume exposure can be used, wherein these 3D models are rotated and displaced until the surfaces of the tooth stumps of these 3D models fit with the surfaces of the tooth stumps from the optical surface monitoring exposures. This method of adjusting the 3D models can also be performed automatically in a computer-assisted process, wherein the surfaces of the tooth stumps of the 3D models are superimposed with the surfaces of the tooth stumps from the optical surface monitoring exposures.

A reliable determination of the position and orientation of the tooth root is thereby ensured by a simple method.

The tooth stumps may be different parts of hard tissue which protrude out of the gingiva and can be detected in an optical exposure. For example, tooth stumps may be complete dental crowns or also just parts of natural or artificial teeth (such as preparations or abutments) protruding out of the gingiva.

In the segmentation process, the initial volume exposure and the subsequent optical surface monitoring exposures are automatically searched for the patterns of the tooth stumps, the tooth roots and/or the implants, and these are segmented from the surrounding tissue.

One advantage of the present method is that the patient is exposed to a dose only during the initial volume acquisition (such as an x-ray), wherein only three-dimensional optical surface monitoring acquisitions of the dental situation are performed for the additional check of the tooth positions. A frequent observation with a low dose exposure is made possible in this way.

The surfaces of the tooth stumps and the position of the tooth roots and/or of the implants may advantageously be determined on the basis of the initial three-dimensional exposure, wherein the positional relationship is determined only on the basis of the volume exposure.

Both the tooth stumps and the tooth roots and/or the implants are thereby detected in the volume exposure, for example by means a segmentation method, wherein the positional relationship is subsequently determined.

To determine the positional relationship, an initial optical surface acquisition of the teeth to be checked may advantageously be performed, wherein the positional relationship between the position of the tooth roots and/or of the implants is determined from the initial volume exposure and the position of the surfaces of the tooth stumps is determined from the initial optical surface exposure.

In this alternative, the positional relationship between the tooth stumps and the tooth roots and/or the implants is determined by comparing the initial volume exposure with the initial optical surface exposure. A simple and error-free determination of the positional relationship is made possible in this way.

The initial volume acquisition and the initial optical surface acquisition may advantageously be implemented within a time period of at most 4 hours during an initial examination.

The positional relationship is thereby also determined at an initial examination date. At follow-up appointments, the position of the tooth roots and/or of the implants is subsequently checked at regular intervals on the basis of the surface monitoring exposures.

The determination of the positional relationship may advantageously be performed manually in a computer-assisted process, wherein the tooth stumps, the tooth roots and/or the implants are selected manually by a user using input means.

In this alternative, the segmentation is performed manually by the user, wherein the user puts a border around the tooth stumps or the tooth roots virtually by means of a cursor using input means, and thus the dimensions as well as the position and orientation relative to one another are determined.

The initial three-dimensional volume acquisition may advantageously be a three-dimensional CT x-ray acquisition.

In particular hard tissue (such as dental tissue and the jawbone) is thereby imaged in a particularly distinct manner.

The initial three-dimensional volume acquisition may advantageously be a three-dimensional MRT acquisition.

Soft tissue (such as gingiva) is thereby imaged particularly distinctly.

The optical surface monitoring acquisition may advantageously be implemented by means of an optical measurement device using a strip projection method.

For example, the optical measurement device may be a dental handpiece which measures the dental situation using the strip projection method and thereby creates a three-dimensional optical exposure.

The optical surface monitoring exposure may advantageously be generated using a digitized impression of the teeth.

Additional optical surface monitoring acquisitions of the teeth to be checked may advantageously be implemented for checking. Starting from the position of the surfaces of the tooth stumps, the position and orientation of the tooth roots and/or of the implants relative to one another and/or relative to a jawbone may subsequently be determined from the optical surface monitoring exposures.

The tooth roots and/or implants determined on the basis of the surfaces of the tooth stumps from the optical surface monitoring exposure may advantageously be presented graphically (by means of a display device) relative to one another and/or in relation to the jawbone from the initial volume image.

For example, the display device may be a monitor which depicts the initial x-ray exposure in superposition with the calculated 3D models of the teeth. This makes it possible for the user to better estimate the orientation of the tooth roots in relation to the jawbone.

The surfaces of the registered tooth stumps from the initial optical exposure may advantageously be stored in a data memory. The additional optical exposures may then be searched automatically for these registered surfaces of the tooth stumps by means of a pattern recognition algorithm, wherein the position and/orientation of the tooth stumps relative to one another and/or relative to the jawbone are subsequently determined automatically in a computer-assisted process.

The search for the surfaces of the tooth stumps in the optical exposures is simplified by using the pattern recognition algorithm.

BRIEF DESCRIPTION OF THE DRAWINGS

The invention is explained on the basis of the drawings, in which.

DETAILED DESCRIPTION OF THE INVENTION

Figure 1:
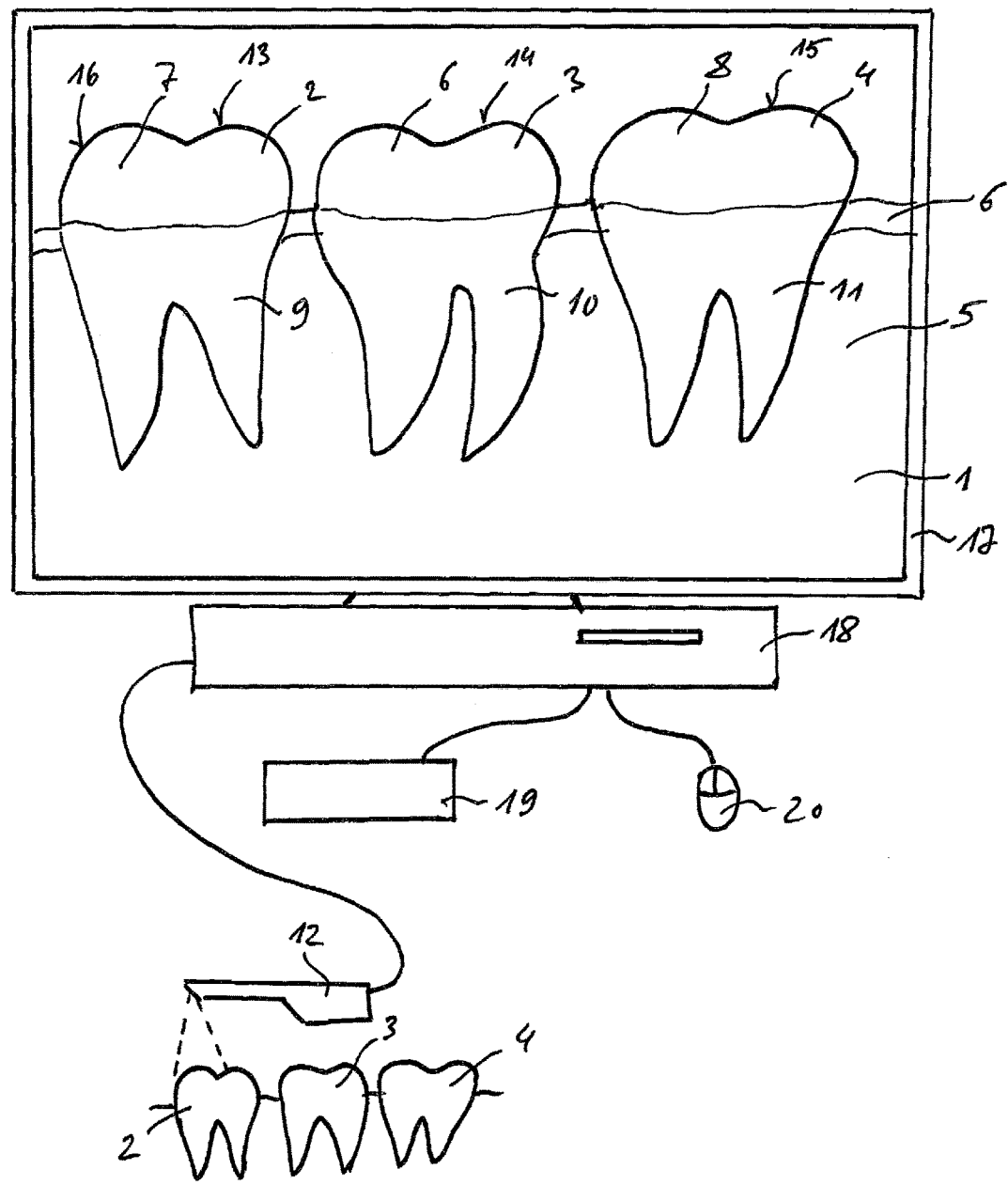
FIG. 1 shows a diagram to clarify the present method.

FIG. 1 shows a diagram for clarification of the present method for checking tooth positions. In the first method, step an initial three-dimensional x-ray exposure 1 is implemented by means of an x-ray system (such as a CT x-ray system). The x-ray exposure includes the teeth 2, 3 and 4 to be checked, as well as the jawbone 5 and a gingival layer 6. On the basis of the initial x-ray exposure 1, the position and orientation of the teeth 2, 3, 4 to be checked, in particular tooth stumps 7, 6 and 8 and/or tooth roots 9, 10 and 11, are then registered. In the next method step, in addition to the initial x-ray acquisition an initial optical acquisition of the teeth 2, 3 and 4 to be checked is implemented by means of the measurement device 12, which may be based on a strip projection method. In the additional method step, a positional relationship is determined between the position of the teeth 2, 3 and 4 to be checked in the initial x-ray exposure 5 and the surfaces 13, 14 and 15 of the tooth stumps 7, 6 and 8 from the initial optical exposure. The initial optical exposure 16 (which includes the tooth situation and in particular the surfaces 13, 14 and 15 of the tooth stumps 7, 6 and 8) is presented by means of a display device 17 (such as a monitor), in superposition with the three-dimensional x-ray exposure 5. The positional relationship between the exposures 5 and 16 is determined in that congruent structures (such as the surfaces 13, 14 and 15 of the tooth stumps 7, 6 and 8) are brought into congruence automatically in a computer-assisted process by means of the computer 18. The determination of the positional relationship may also as an alternative be performed manually by a user using the input means, such as a keyboard 19 and a mouse 20. In the additional method step, the position and orientation of the tooth roots 9, 10 and 11 relative to one another and/or relative to the jawbone 5 are calculated using the determined positional relationship based on the position of the surfaces 13, 14 and 15 of the tooth stumps 7, 6 and 8 from the optical exposure 16. Additional optical three-dimensional exposures of the teeth 2, 3 and 4 to be checked are subsequently taken by means of the measurement device 12 at regular time intervals. Based on the position of the surfaces 13, 14 and 15, the altered position and orientation of the tooth roots 9, 10 and 11 relative to one another and/or relative to the jawbone 5 are then calculated. The registration of the tooth stumps 6, 7 and 8 in the initial x-ray exposure and the initial optical exposure, as well as the registration of the tooth roots 9, 10 and 11 in the initial x-ray exposure, can take place by means of a segmentation method which analyzes the exposures by means of the computer 18 and segments the teeth 2, 3 and 4. The segmented teeth 2, 3 and 4 may also be stored as 3D models in a data memory, wherein the additional optical exposures may be searched for these 3D models of the teeth by means of a pattern recognition algorithm.

Figure 2:
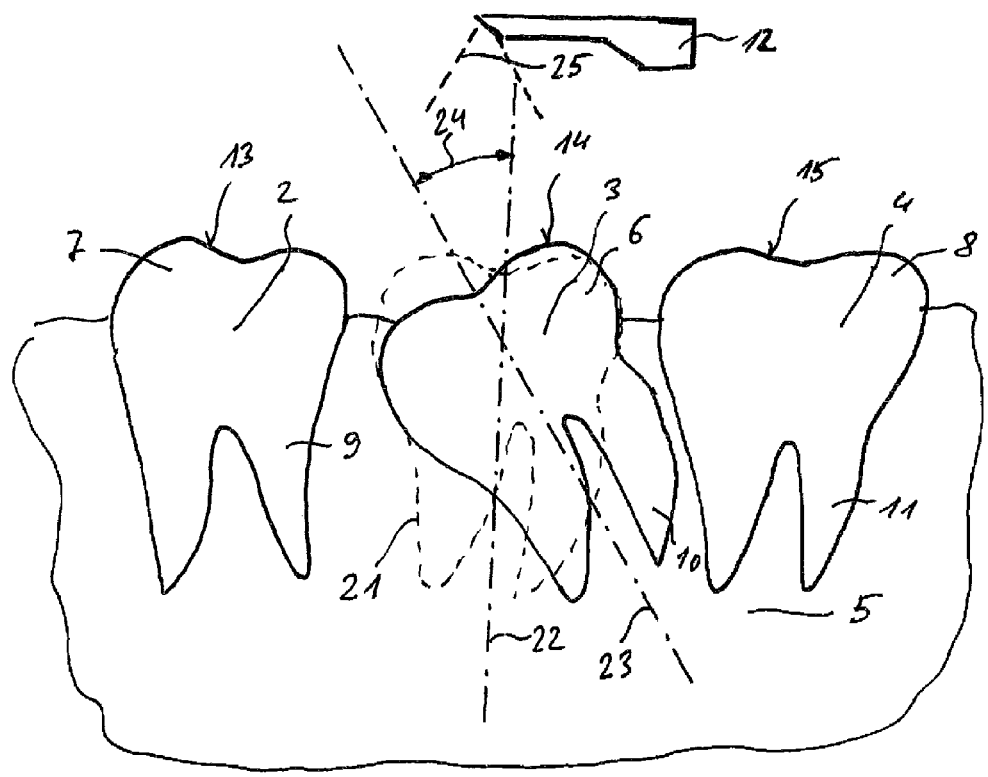
FIG. 2 shows a diagram to clarify the present method, wherein a tooth is rotated and displaced in comparison with FIG. 1.

FIG. 2 shows a diagram to clarify the present method, wherein the middle tooth 3 has rotated and shifted relative to the neighboring teeth 2 and 4 and relative to the jawbone 5 in comparison with FIG. 1. The original position and orientation of the tooth 3 is represented by the dashed line 21. A central axis of the middle tooth 3 has thus been shifted by an angle 24 from an original position 22 to a new position 23. To check the tooth positions, an optical surface monitoring acquisition 25 is implemented by means of the measurement device 12 from FIG. 1, wherein the surfaces 13, 14 and 15 of the tooth stumps 7, 6 and 8 are detected again. Starting from the position of the surfaces 13, 14 and 15, the position and orientation of the tooth roots 9, 10 and 11 relative to one another and/or relative to the jawbone 5 are subsequently calculated. In this way, multiple surface monitoring acquisitions can therefore be implemented at short time intervals to permit a precise checking of the tooth positions with only a low dose exposure.

REFERENCE NUMERALS

1 Initial x-ray exposure
2 First tooth
3 Second tooth
4 Third tooth
5 Jawbone
6 Dental crown
7 Dental crown
8 Dental crown
9 Tooth root
10 Tooth root
11 Tooth root
12 Measurement device
13 First surface of the dental crown
14 Second surface of the dental crown
15 Third surface of the dental crown
16 Initial optical exposure
17 Display device, monitor
18 Computer
19 Keyboard
20 Mouse
21 Dashed line
22 Original position
23 New position
24 Angle
25 Optical surface monitoring exposure

The invention claimed is:
1. A method for checking tooth positions, the method comprising:
determining a positional relationship between a surface of a tooth stump and a position of a tooth root or implant based on three-dimensional volume data from an initial radiographic exposure,
wherein (i) the tooth stump and the tooth root are part of a same tooth, or (ii) the tooth stump is attached to the implant;
calculating an initial position and orientation of the tooth root or implant relative to a jawbone using the positional relationship between the surface of the tooth stump and the position of the tooth root or implant; and
calculating an altered position and orientation of the tooth root or implant relative to the jawbone using (i) non-radiographic data of the surface of the tooth stump acquired after the initial radiographic exposure, and (ii) the determined positional relationship between the surface of the tooth stump and the position of the tooth root or implant,
wherein the altered position and orientation of the tooth root or implant is different from the initial position and orientation of the tooth root or implant.
2. The method according to claim 1, further comprising:
generating a three-dimensional model of the tooth stump and the tooth root or implant based on the three-dimensional volume data from the initial radiographic exposure; and
rotating and/or displacing the three-dimensional model until a surface of the three-dimensional model corresponding to the tooth stump fits with a surface of the tooth stump in the non-radiographic data.
3. The method according to claim 1, wherein the determining of the positional relationship between the surface of the tooth stump and the position of the tooth root or implant is also based on initial optical image data of an initial optical image of the surface of the tooth stump.
4. The method according to claim 3, wherein the three-dimensional volume data and the initial optical image data are generated within a time period of 4 hours or less.
5. The method according to claim 1, wherein the three-dimensional volume data is generated by three-dimensional CT x-ray acquisition.
6. The method according to claim 1, wherein the three-dimensional volume data is generated by three-dimensional MRI acquisition.
7. The method according to claim 1, wherein the non-radiographic data is optical image data generated by an optical measurement device using a strip projection method.
8. The method according to claim 1, wherein the non-radiographic data is generated from a digitized impression of the tooth.
9. The method according to claim 1, further comprising:
displaying on a display device the altered position and orientation of the tooth root or implant relative to the jawbone.
10. The method according to claim 1, further comprising:
registering the surface of the tooth stump in the three-dimensional volume data from the initial radiographic exposure; and
searching the non-radiographic data for the registered surface of the tooth stump using a pattern recognition algorithm.
11. An apparatus for checking tooth positions, the apparatus comprising:
a computer configured to:
determine a positional relationship between a surface of a tooth stump and a position of a tooth root or implant based on three-dimensional volume data from an initial radiographic exposure, wherein (i) the tooth stump and the tooth root are part of a same tooth, or (ii) the tooth stump is attached to the implant;

calculate an initial position and orientation of the tooth root or implant relative to a jawbone using the positional relationship between the surface of the tooth stump and the position of the tooth root or implant; and calculate an altered position and orientation of the tooth root or implant relative to the jawbone using (ii) non-radiographic data of the surface of the tooth, acquired after the initial radiographic exposure, and (ii) the determined positional relationship between the surface of the tooth stump and the position of the tooth root or implant wherein the altered position and orientation of the tooth root or implant is different from the initial position and orientation of the tooth root or implant.

12. The apparatus according to claim 11, wherein the positional relationship between the surface of the tooth stump and the position of the tooth root or implant is further determined based on initial optical image data of an initial optical image of the surface of the tooth stump.

13. The apparatus according to claim 12, wherein the three-dimensional volume data and the initial optical image data are generated within a time period of 4 hours or less.

14. The apparatus according to claim 11, wherein the three-dimensional volume data is generated by three-dimensional CT x-ray acquisition.

15. The apparatus according to claim 11, wherein the three-dimensional volume data is generated by three-dimensional MRI acquisition.

16. The apparatus according to claim 11, wherein the non-radiographic data is optical image data generated by an optical measurement device using a strip projection method.

17. The apparatus according to claim 11, wherein the non-radiographic data is generated from a digitized impression of the tooth.

18. The apparatus according to claim 11, further comprising:

a display device, wherein the computer is further configured to cause the display device to display the altered position and orientation of the tooth root relative to the jawbone.

19. The apparatus according to claim 11, wherein the computer is further configured to:

register the surface of the tooth stump in the three-dimensional volume data from the initial radiographic scan; and search the non-radiographic data for the registered surface of the tooth stump using a pattern recognition algorithm.

* * * * *